United States Patent [19]

Ahnell et al.

[11] 4,073,691
[45] Feb. 14, 1978

[54] METHOD FOR DETECTING THE PRESENCE OF BIOLOGICALLY ACTIVE AGENTS

[75] Inventors: Joseph E. Ahnell, Baltimore; Rodney L. Broman, Falston; John R. Waters, Towson, all of Md.

[73] Assignee: Johnston Laboratories, Inc., Cockeysville, Md.

[21] Appl. No.: 717,351

[22] Filed: Aug. 24, 1976

[51] Int. Cl.² .............................................. C12K 1/04
[52] U.S. Cl. ........................... 195/103.5 M; 195/127
[58] Field of Search ................. 195/103.5 R, 103.5 M

[56] References Cited

U.S. PATENT DOCUMENTS

| 3,838,034 | 9/1974 | Groves | 195/103.5 M |
| 3,907,646 | 9/1975 | Wilkins et al. | 195/103.5 M |
| 3,935,073 | 1/1976 | Waters | 195/103.5 M |

Primary Examiner—Alvin E. Tanenholtz
Assistant Examiner—C. A. Fan
Attorney, Agent, or Firm—Schuyler, Birch, Swindler, McKie & Beckett

[57] ABSTRACT

A sample of material to be tested for the presence of biologically active agents, such as bacteria, is introduced into a sealable container partially filled with a culture medium; the remainder of the container being filled with a culture gas, the container and its contents are subjected to conditions conducive to biological activity for a predetermined period sufficient for fermentation of the medium to produce at least one gaseous product after which the character of the culture gas in the container is determined and compared to the initial character of the culture gas in order to detect any differences caused by changes in the composition of the culture gas indicating the presence or absence of biologically active agents in the sample.

15 Claims, 3 Drawing Figures

METHOD FOR DETECTING THE PRESENCE OF BIOLOGICALLY ACTIVE AGENTS

BACKGROUND OF THE INVENTION

In many fields of endeavor it is important to be able to determine whether or not substances are contaminated with biologically active agents such as bacteria and the like. Examples of such fields are the medical field, the food processing industry, the pharmaceutical industry, the cosmetics industry, the field of public health, and the preparation of interplanetary space vehicles.

In the past, it has been a standard practice to place a sample of a material to be tested for the presence of biologically active agents in an appropriate growth medium on a Petri dish and to make visual observations of the resulting microbial growth, if any. Not only are such culturing methods slow and laborious, but because they depend on the subjective judgment of individual human observers, the result obtained is not uniformly reliable.

Techniques have also been developed for detection of bacteria which involve incubation of a sample of material to be tested in a closed container with a radioactive isotope labeled culture medium and monitoring the atmosphere in the container above the medium to determine whether or not radioactive gases are produced. A system of this type is disclosed in U.S. Pat. Nos. 3,676,679 and 3,935,073. Such systems are rapid and reliable, but they suffer from a number of disadvantages. In the first place, radioactively labeled materials are not inexpensive and require special handling during storage, use and disposal. Moreover, although the levels of radioactivity encountered in using such systems are very low, prospective users may be deterred by personal fears of radioactivity. The use of radioactive isotopes in instrumental systems has generally been considered necessary in order to facilitate detection of minute quantities of metabolic product gases thereby to detect the presence of biologically active species. There exists a need for an instrumental system for measuring metabolically produced non-radioactive gases to detect bacteria and the like.

Accordingly, it is an object of the present invention to provide a rapid method for detecting the presence or absence of biologically active agents.

Another object of the invention is to provide a method for detecting the presence or absence of biologically active agents which uses comparatively inexpensive materials.

It is a further object of the present invention to provide an instrumental method for detecting the presence or absence of biologically active agents which is not subject to the vagaries of subjective human observations.

Another object of the present invention is to provide an instrumental system for detecting the presence or absence of biologically active agents which avoids the use of radioactive materials.

Further objects of the invention will be apparent from a consideration of the following description.

SUMMARY OF THE INVENTION

These and other objects of the invention are achieved by providing a method for detecting the presence of biologically active agents comprising the steps of providing a sealable sterile container containing a sterile non-radioactive culture medium and a quantity of culture gas of known character in said container above said culture medium, said container comprising means for introducing a test material into the container; introducing a sample of material to be tested for biological activity into the container and sealing the container; subjecting the sealed container to conditions conducive to biological activity for a predetermined period of time sufficient for fermentation of the culture medium to produce at least one gaseous product, and thereafter testing the character of the culture gas in said container and comparing the character of the culture gas after exposure of the container and its contents to conditions conducive to biological activity to the initial character of the culture gas.

In one preferred embodiment, the initial carbon dioxide content of the culture gas and the carbon dioxide content of the culture gas after exposure of the container and contents to conditions conducive to biological activity are determined by withdrawing samples of the culture gas before and after subjection to conditions conducive to biological activity, taking a mass spectrum of each culture gas sample and comparing the relative intensities of the M/e 44 peaks of the two spectra which represent the amounts of carbon dioxide present in the gas samples to the intensities of the M/e peaks of the respective spectra corresponding to the molecular weight of an inert reference gas, such as argon, which is present at a constant level in the culture gas.

DETAILED DESCRIPTION OF THE PREFERRED EMBODIMENTS

Figure 1:
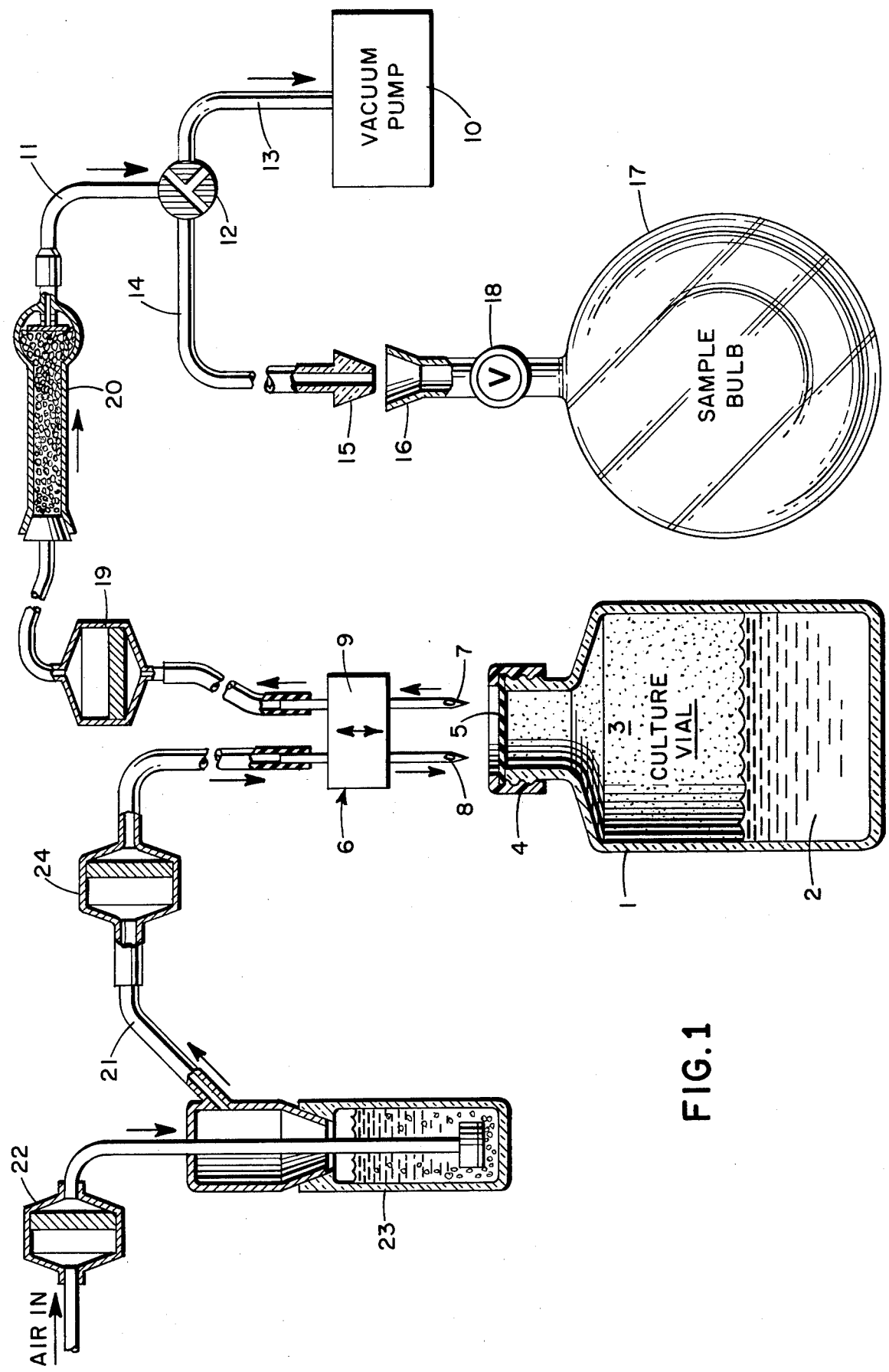
FIG. 1 is a schematic representation of apparatus utilized in practicing the method of the invention.

Turning now to FIG. 1, reference numeral 1 designates a culture vial utilized in the practice of the method of the present invention. Vial 1 is partially filled with a culture medium 2. Typical culture media generally contain water, a carbon source, a nitrogen source, calcium, magnesium, potassium, phosphate, sulfate, and trace amounts of other minor elements. The carbon source may be a carbohydrate, amino acid, mono- or dicarboxylic acid or salt thereof, polyhydroxy alcohol, hydroxy acid or other metabolizable carbon compound. Usually the carbon source will comprise at least one sugar such as glucose, sucrose, fructose, xylose, maltose, lactose etc. Amino acids such as lysine, glycine, alanine, tyrosine, threonine, histidine, leucine, etc. also frequently comprise part of the culture media carbon source.

The nitrogen source may be nitrate, nitrite, ammonia, urea or any other assimilable organic or inorganic nitrogen source. An amino acid might serve as both a carbon and a nitrogen source. Sufficient nitrogen should be present to facilitate cell growth.

A variety of calcium, potassium and magnesium salts may be employed in the culture medium including chlorides, sulfates, phosphates and the like. Similarly, phosphate and sulfate ions can be supplied as a variety of salts. As such materials are conventional in fermentation media, the selection of specific materials as well as their proportions is thought to be within the skill of the art.

The so called minor elements which are present in trace amounts are commonly understood to include manganese, iron, zinc, cobalt and possibly others.

Due to the fact that most biologically active species cannot function in strongly acidic or strongly alkaline media, suitable buffers such as potassium or ammonium phosphates may be employed, if desired, to maintain the pH of the culture medium near neutral.

Examples of well known culture media which may be used in the present invention are peptone broth, tryptic soy broth, nutrient broth, thioglycolate broth, or brain-heart infusion broth.

As noted previously, culture medium 2 fills only a portion of vial 1. The remainder of the vial is filled with gas referred to herein as the culture gas. The culture gas may be any gas or mixture of gases which will support the growth of biologically active agents. Under most circumstances, ordinary air provides an acceptable culture gas for aerobic organisms. Cylinder gas may be utilized as the culture gas instead of ambient air. When anaerobic bacteria are of interest, the culture gas should be oxygen free. A nitrogen and carbon dioxide culture gas may be used for anaerobic organisms. Reference numeral 3 is utilized to designate the culture gas. Vial 1 with the medium and culture gas therein is sealed with a cap 4. In the illustrated embodiment, cap 4 comprises a self-sealing rubber septum which allows material to be injected into or removed from the vial through hollow needles. The sealed vials with culture medium and culture gas inside are sterilized in an autoclave to prevent disruption of tests by biologically active agents from sources other than the test material.

To initiate the testing of a material for the presence of biologically active agents, a sample of the material is introduced into a sterile vial containing culture medium and culture gas. If the sample is a fluid, such as blood or urine, introduction of the sample can be effected by injecting it through septum 5 with a hypodermic needle. Care should be taken to sterilize the needle and the septum before making the injection in order to prevent contamination of the test vial. Solid materials may be tested by utilizing vials provided with apertures through the vial walls closed by tightly sealing, removable and replaceable caps.

After inoculation with the test material, the inoculated vial is incubated, i.e. subjected to conditions conducive to biological activity, for a predetermined period of time sufficient for fermentation of the culture medium to produce at least one gaseous product. It should be noted that the terms "ferment" and "fermentation" are not used herein in any technically restrictive sense, but are intended to refer to metabolic activity generally, including without limitation the action of bacteria, yeasts, fungi, algae, protozoa, viruses, active enzymes and the like. If photoresponsive or phototoxic microorganisms are of interest, light should be provided or excluded accordingly.

Since most medically significant bacteria achieve their maximum growth rates at temperatures of approximately 36° C plus or minus 1° C, the culture vials are desirably maintained at a temperature lying in the range from about 35° C to about 37° C. It is understood, however, that not all biologically active agents exhibit maximum growth within the recited temperature range. If it is of particular interest to determine whether or not a specific microorganism which grows better at some other temperature is present, then the temperature should be maintained at approximately that temperature at which the organism in question exhibits maximum growth.

Agitation of the culture medium also is useful both to promote growth of biologically active agents which may be present and also to liberate carbon dioxide, hydrogen sulfide or other gases produced by the metabolic activity of biologically active agents from the culture medium into the culture gas. A conventional shaking table may be utilized to effect gentle agitation. Alternatively, the culture medium can be stirred with a magnetic stirring bar magnetically coupled to a rotating magnet disposed beneath the culture vial.

The length of the incubation period before the character of the culture gas is tested and/or between subsequent tests depends on the particular application. Under favorably controlled conditions, the method of the invention is capable of detecting positive test results much more rapidly than conventional culturing techniques.

In medical testing, positive test results may be observed after less than eight hours, in some cases with 2 to 4 hours after inoculation. Therefore in medical laboratories, it may be desirable to test the character of the culture gas after intervals as short as one hour, repeating the test periodically either until positive results are observed or until it safely can be concluded that the sample is negative. The rapidity of the method of the invention is of particular advantage in the medical field where prompt results can be a matter of life or death.

In testing samples from batches of processed food products for bacterial contamination, repeated testing is neither necessary or desirable. In such situations it is preferred to make a single test of the character of the culture gas after a sufficiently long incubation period that there is a high probability that gas production has reached detectable levels in all positive samples. Incubation periods are limited by the capacity to store batches of processed products while awaiting the results of the tests of the samples and may range as long as 24 to 48 hours or longer.

After a short period of incubation, any bacteria or other biologically active agent present in the sample will begin to grow in the culture medium thereby consuming nutrients from the medium and producing metabolic byproducts. Gaseous byproducts such as $CO_2$ or $H_2S$ will diffuse out of the culture medium into the culture gas. After a sufficient period of incubation for an appreciable amount of gas to be formed, a sample of the culture gas is taken and the character of the sample is tested. Testing of the character of the culture gas may involve a complete determination of the composition of the gas or merely a determination of the relative proportion of one or more constituents of the gas or even measurement of one or more properties of the gas, such as optical absorption or thermal conductivity, which are affected by changes in the composition of the gas. After taking a culture gas sample, the vial and contents may be reincubated for additional periods, and the culture gas resampled and retested after each period, if desired.

FIG. 1 also schematically illustrates apparatus used for sampling the culture gas in a culture vial. The apparatus comprises a needle assembly generally designated by reference numeral 6 consisting of two hollow needles 7 and 8 respectively mounted in a stainless steel holder 9. Needle 7 is referred to as the outlet needle and is connected to a vacuum pump 10 by means of line 11, valve 12 and line 13. Valve 12 is also connected to line 14 which leads to a tapered fitting 15 adapted to engage a mating fitting 16 at the mouth of a removable sample bulb 17. A valve 18 is provided to close off the inlet of sample bulb 17.

The preferred procedure for sampling the culture gas begins by mating fittings 15 and 16 to secure sample bulb 17 to the needle assembly. Valve 12 is switched to connect lines 13 and 14, vacuum pump 10 is turned on and valve 18 is opened so that sample bulb 17 is evacuated. When all of the contents of bulb 17 have been removed by pump 10, valve 12 is switched to a closed position in which none of the lines 11, 13 and 14 are connected with each other. Needles 7 and 8 and septum 5 are sterilized, e.g., by wiping with 70% isopropanol and either burning off the alcohol in a flame or allowing it to evaporate, and the needle assembly 6 is forced against cap 4 until needles 7 and 8 penetrate septum 5. Sterilization of the septum and needles prevents contamination of culture medium 2 in vial 1. Once the needles have been inserted through the septum, valve 12 is switched to a position connecting lines 11 and 14 whereupon culture gas 3 from vial 1 passes into the evacuated sample bulb through needle 7, line 11, valve 12, line 14, joints 15 and 16 and valve 18. A submicron filter 19 interposed in line 11 prevents any of the culture medium which may have been sucked up along with the culture gas from passing into sample bulb 17. Line 11 is also provided with a drying tube 20 filled with silica gel or other suitable drying agent to remove excess moisture from the culture gas sample. Replacement gas enters vial 1 through line 21 and inlet needle 8. A submicron filter 22 interposed in line 21 prevents dust, airborne bacteria and other contaminants from entering the culture vial with the replacement gas.

It will be appreciated, particularly in the medical field, that prompt results and consequently short incubation times are highly desirable. At the same time, it will be appreciated that the shorter the incubation period, the less growth will take place in the culture and the less carbon dioxide or other metabolic byproduct gas will be produced. Consequently if carbon dioxide is being measured, it is desirable to be able to detect very small changes in carbon dioxide concentration of the culture gas. Since small changes may be more readily detected when there is a lower base level of carbon dioxide in the culture gas, it may be desirable to pass incoming culture gas through a carbon dioxide trap to reduce the carbon dioxide content of the fresh culture gas to a low level. The use of a carbon dioxide trap also tends to level out fluctuations in carbon dioxide content which may occur in the ambient atmosphere if ambient air is used as the culture gas. One possible arrangement is illustrated schematically in FIG. 1 wherein replacement culture gas (air) entering the culture vial through line 21 and needle 8 passes through a carbon dioxide trap 23. A molecular sieve or a soda lime preparation may be used as the $CO_2$ trap. Submicron filter 24 is interposed in line 21 between the carbon dioxide trap 23 and needle 8 to prevent material from the carbon dioxide trap from being drawn into vial 1 with the replacement air. However, it should be noted that low levels of $CO_2$ are not essential; satisfactory detection of the presence or absence of biologically active agents can be carried out utilizing synthetic culture gases containing as much as 5% carbon dioxide. Similar considerations apply when gases other than carbon dioxide are measured.

Once sample bulb 17 is filled, valve 18 is closed and the sample bulb containing the culture gas sample can be removed for analysis. Use of a sample bulb having a substantially larger volume than the volume of the gas space in the culture vial enables substantially complete collection of the culture gas from the culture vial for subsequent testing and correspondingly substantially complete replacement of the old culture gas from the culture vial with new culture gas. When repeated tests are carried out at periodic intervals on a single sample vial, it is possible in this way to provide a fresh culture gas atmosphere for each time segment. It should be noted, however, that complete replacement of the culture gas in the vial is not essential. It is considered within the scope of the invention to sample and test small portions of the culture gas within each vial.

Since very small differences in gas content are being measured and since the temperature of the culture medium can significantly affect the solubility of gases in the medium, for maximum accuracy care should be taken to ensure that all vials in a given test are at the same temperature when culture gas samples are taken.

Testing of the character of the culture gas sample can be carried out in several different ways. One particularly preferred procedure for testing the culture gas sample is to take a mass spectrum of the gas sample and compare the relative peak heights of the M/e values corresponding to the molecular weights of the constituent gases. Variations in sample size and mass spectrometer efficiency between various samples can be compensated for by proportionately adjusting the relative peak heights of one spectrum until the spectrum peaks for an inert reference gas present in substantially constant concentration are equal and then comparing the heights of corresponding peaks. A preferred inert reference gas is argon. Because of its chemically inert nature, argon is neither produced nor consumed by the metabolic action of biologically active agents and therefore remains at substantially constant concentration at all times. Other inert gases, such as neon, could also be used as the reference gas.

Naturally, testing of the character of the culture gas need not be limited to analysis of the composition of the gas with a mass spectrometer. Instead, any suitable means of analyzing the composition of the gas or measuring the properties of the culture gas affected by changes in composition may be utilized.

Gas chromatography is considered particularly advantageous for medical laboratory instruments because the gas chromatograph is a comparatively uncomplex and inexpensive piece of apparatus; its use does not require highly skilled operators and the operation of gas chromatographs is consistent and reliable under a comparatively wide range of operating conditions. Moreover, analysis by gas chromatograph is comparatively prompt. Adequate separations of culture gas components are possible using column retention times on the order of 1 to 20 minutes. If it is desired to monitor the carbon dioxide content of the culture gas, a gas chromatograph with a thermal conductivity detector may be utilized with helium as the carrier gas. Carbon dioxide may also be monitored by catalytically reducing the carbon dioxide to methane and using a hydrogen flame ion detector with nitrogen as the carrier gas. Hydrogen sulfide gas may be monitored using either a sulfur specific flame photometric detector or an electron capture detector with nitrogen as the carrier gas.

Additional methods of testing the character of the culture gas which may be used include measurements of infrared absorption, thermal-conductivity, dielectric constant, velocity of sound and other properties which are affected by changes in the gas composition.

While testing the character of the culture gas by means of a mass spectrometer or a gas chromatograph requires withdrawal of at least a part of the culture gas from the culture vial, it is, of course, possible to test the character of the culture gas without withdrawing any of the gas from the vial by inserting an appropriate analytical probe into the culture vial through a self-sealing rubber septum. For example, various properties of the culture gas affected by changes in the culture gas composition could be measured using a thermal conductivity probe, a piezoelectric probe, a gaseous specific ion electrode probe or a spectrometric light pipe probe without withdrawing any of the culture gas from the test vial.

Each culture gas sample is tested to determine whether the character of the gas has been affected by the presence of metabolic byproducts. A change in the character of the culture gas may be attributed to a change in the composition of the gas as a result of the metabolic activity of a biologically active agent present in the inoculum. Testing the character of the culture gas does not mean that it is essential to conduct a total analysis of the gas, i.e. to measure the relative amount of each and every constituent of a culture gas mixture, rather it may be sufficient if the relative content of at least one gaseous metabolic product is measured or if some physical property which is affected by the appearance of metabolic byproduct gases in the culture gas is measured. A preferred procedure is to measure the relative content of carbon dioxide which is produced from fermentable organic substances by the metabolic action of a vast number of biologically active agents. Another measurable gas produced by the metabolic action of many biologically active agents is hydrogen sulfide. Other comparatively common gases which may be useful for more or less general detection of biologically active agents include methane, ammonia, formaldehyde, acetic acid, hydrogen and oxygen. Monitoring the culture gas content of less common metabolic product gases may be particularly useful for detection of specific types of microorganisms. Such gases include methyl amine, methyl mercaptan, butanol, butyric acid, putrescine, cadaverine, ethane and sulfur dioxide.

When carbon dioxide is being measured and no subsequent measurements of the carbon dioxide content of a particular vial are contemplated, then the culture medium may be acidified by an injection of a small amount of acid such as hydrochloric or sulfuric to release carbon dioxide from solution in the medium into the culture gas atmosphere thereby to provide a more sensitive test.

The method of the invention requires a comparison of the character of a culture gas from an incubated test vial to a reference standard representing the initial character of the culture gas in order to detect changes in composition of the culture gas due to the production of one or more metabolic byproduct gases by one or more biologically active agents in the medium. The reference standard may be developed either by direct measurement of the initial culture gas composition prior to incubation of the test vial or by simultaneously measuring the gas from an uninoculated control vial initially containing the same culture gas after subjection to a parallel incubation treatment. The latter procedure has the advantage of compensating for any gases produced by thermal degradation of the culture medium during the incubation period and of allowing all measurements to be made at one time. The former procedure has the advantage of requiring only a single culture vial. If cylinder gas is used as the culture gas, it may not be necessary to redetermine the initial character of the culture gas with each test. Instead, a single test of the gas from a given cylinder may be used as the reference standard for all tests run with gas from that cylinder.

An appreciable difference between the character of the post-incubation culture gas sample and the initial culture gas character indicates the presence of some biologically active agent in the test material. By an appreciable difference is meant a difference greater than the ordinary maximum statistical deviation to be expected for the analytical technique used to measure the character of the culture gas or attributable to minor variations in experimental conditions, e.g. vial temperature, between identical samples.

When analysis of the composition of the culture gas samples is carried out by taking mass spectra of the gas samples and comparing the relative heights of the carbon dioxide and argon peaks, the worst case probable error can be estimated at less than plus or minus 6%. Differences in carbon dioxide concentration greater than twice this amount can therefore be considered appreciable.

EXAMPLE I

Figure 2:
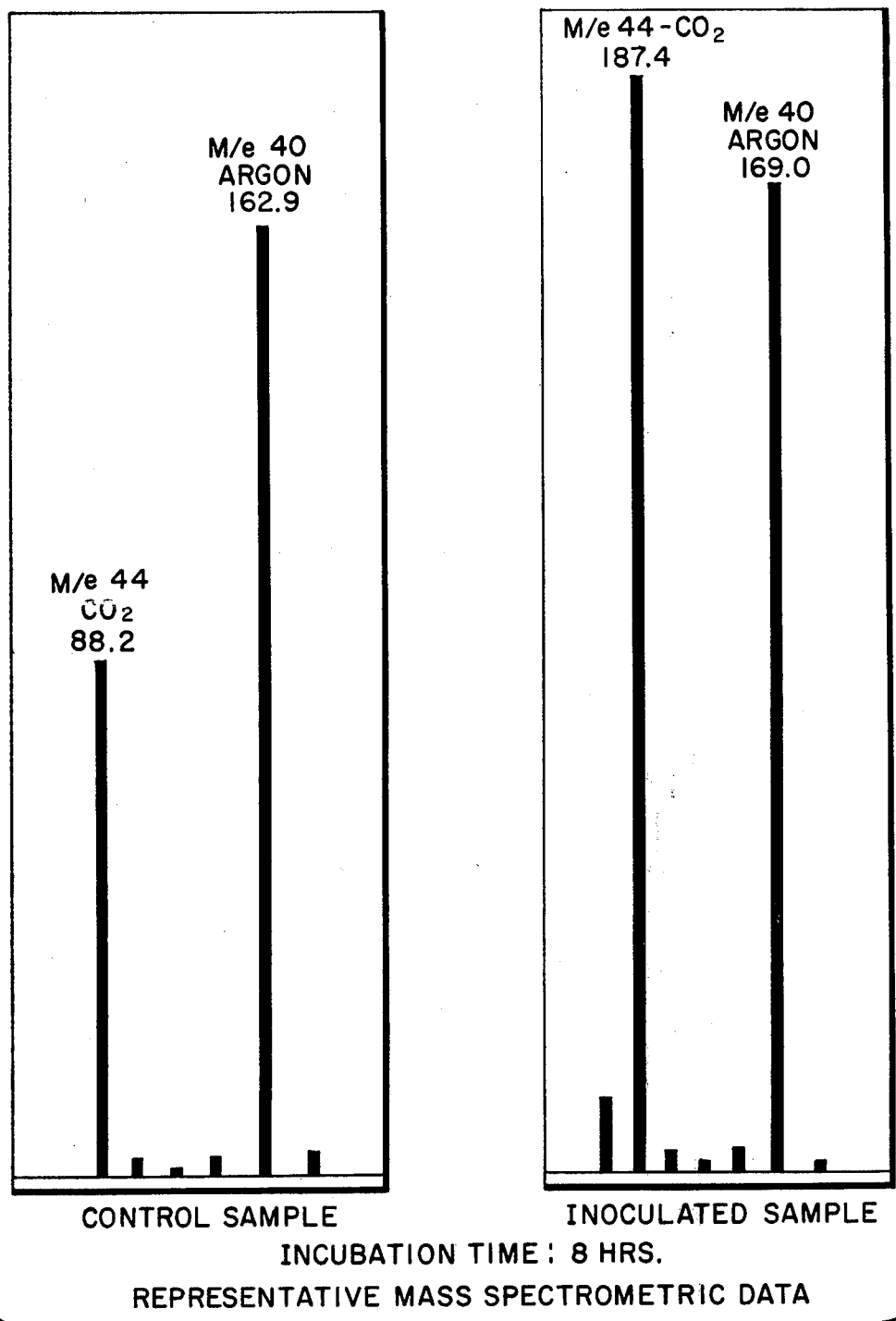
FIG. 2 depicts representative mass spectrometric data from an actual test of the invention.

FIG. 2 shows comparative mass spectra of culture gas taken from an uninoculated control vial and a vial inoculated with an overnight culture of *Pseudomonas pseudoalkaligenes*. The size of each inoculum was 0.5 ml. Each culture vial was a standard 50cc vial containing approximately 30 ml tryptic soy broth culture medium. Both the control sample and the inoculated sample were incubated for a period of 8 hours at 37° C with mild agitation before withdrawal of the culture gas samples whose spectra are shown in FIG. 2. Spectra were taken with a Perkin-Elmer Hitachi model RMU-6 mass spectrometer. Operating parameters of the spectrometer are given in Table I:

TABLE I

| Mass Spectrometer Parameters |
|---|
| Electron Energy = 70eV |
| Ionization (Target) Current = 50 $\mu$ A |
| Mass Range = 450 a.m.u. |
| Accelerating Voltage = 2450V. |
| Head Amplifier Setting = X10 |
| Ion Multiplier High Voltage = 1.5KV, 1.75KV |
| Ion Entrance Slit = 0.19 mm |
| Ion Exit Slit = 1.00 mm |
| Magnet Scan Rate = 6 |
| Start Scan Set: Coarse = 140, 240 |
|     Fine = 0,0 |
| Background Analyzer Pressure = 1.8 $\times 10^{-7}$ mmHg |
| Analyzer Pressure with Sample = 7.5 $\times 10^{-7}$ mmHg |
| Recorder Sensitivity: 1.0V, 0.5V, 0.2V, 0.1V |
|     0.05V, 0.02V |
| Recorder X-Axis Drive = 20 mm/min |
| Gas Sample System Pressure = 6 mmHg |
| Sampling Sub-volume filled, emptied |
|   4 times into reservoir |

It will be seen from FIG. 2 that the M/e 40 (argon) peak heights are very similar for the two samples while there is a substantial difference between the M/e 44 (carbon dioxide) peak heights. Numerical values for the peak heights after substracting out the spectrometer background intensity are shown in Table II:

TABLE II

| Sample | Argon Peak Height | CO₂ Peak Height |
|---|---|---|
| Uninoculated Vial | 162.9 | 88.2 |
| Inoculated Vial | 169.0 | 187.4 |

After proportionally multiplying the peak heights of each spectrum in order to adjust the heights of the argon peaks to a normalized value of 200, the comparative values for the carbon dioxide peaks are 108 and 222 for the uninoculated and inoculated vials respectively. The greater intensity of the carbon dioxide peak in the spectrum of the culture gas sample from the inoculated vial indicates a greater concentration of carbon dioxide in that vial. A mass spectrum of atmospheric air passed through the sampling system yielded a value for the $CO_2$ peak of 83 when the argon peak was normalized to a value of 200. It is apparent that the concentration of carbon dioxide in the control vial culture gas is not much greater than in atmospheric air but that there has been a significant increase in the concentration of carbon dioxide in the inoculated vial. The greater concentration of carbon dioxide in the inoculated vial indicates the presence of a biologically active agent in that vial.

EXAMPLE II

A tryptic soy broth culture medium as prepared by adding 27.5 grams of tryptic soy broth produced by Bioquest (BBL), Cockeysville, Md., to sufficient deionized water to produce 1 liter of medium. Thirty ml. aliquots of medium were dispensed into eight 50 ml vials. The vials were each capped with self-sealing rubber septa, and 0.5 ml of a sterile 60 milligram per ml glycine solution was injected into each vial to enrich the culture medium. The culture media containing vials were then sterilized in an autoclave for 15 minutes at 15 psig. Four of the bottles were then each inoculated with 0.5 ml of an overnight culture of *Pseudomonas pseudoalkaligenes*. Inoculated vials were assigned even numbers, and control vials were assigned odd numbers. Immediately after inoculation the gas space of each vial was flushed with ambient air to provide a fresh culture gas atmosphere in each vial and ensure that all vials had a substantially identical culture gas atmosphere. Before entering the vial, the flushing gas was passed through a submicron filter to remove dust and airborne bacteria and through a carbon dioxide trap consisting of a bubble tower containing 2 molar sodium hydroxide to stabilize the carbon dioxide content. All eight test bottles were then incubated at 35° C with gentle agitation provided by mechanical shaking. The culture gas of vials 1 and 2 was immediately sampled and analyzed with a mass spectrometer to determine the initial carbon dioxide content. The culture gas atmospheres of vials 2, 3 and 4 were sampled after 4 hours incubation, and a mass spectrum was taken of each sample to measure the carbon dioxide content. After 8 hours incubation, the culture gases of vials 2, 5 and 6, and after 12 hours incubation, the culture gases of vials 2, 7 and 8 were sampled and analyzed in like manner.

A 250 ml sample bulb was utilized. The larger volume of the sample bulb in comparison with the approximately 30 ml gas space of the culture vial ensures substantially complete withdrawal of the culture gas from the vial for measurement and in retested vials makes it possible to start each segment of the incubation period with fresh culture gas. Spectrum peak heights were proportionally adjusted to begin the argon peaks to a normalized peak height of 200 mm and the heights of the carbon dioxide peaks were measured.

TABLE III

| | Uninoculated Controls | | Inoculated Test Samples | | Retested Inoculated Sample | |
|---|---|---|---|---|---|---|
| Hours | Sample No. | CO₂ Peak Height mm | Sample No. | CO₂ Peak Height mm | Sample No. | CO₂ Peak Height mm |
| 0 | #1 | 84 | #2 | 53 | — | — |
| 4 | #3 | 85 | #4 | 120 | #2 | 119 |
| 8 | #5 | 86 | #6 | 192 | #2 | 226 |
| 12 | #7 | 87 | #8 | 154 | #2 | 263 |

After 6 hours incubation, a sample of ambient air passed through the filter and carbon dioxide trap was taken and its carbon dioxide content measured to provide a base reference value for the initial culture gas carbon dioxide content. After normalizing the argon peak of the spectrum to a height of 200 mm, the carbon dioxide peak height for the ambient air spectrum was 83 mm. Carbon dioxide peak height values listed in Table III were each compared to the base reference value for ambient air by calculating the ratio of the carbon dioxide peak height from each vial to the normalized carbon dioxide peak for the ambient atmosphere sample. The resulting ratios are shown in Table IV and plotted graphically in FIG. 3.

TABLE IV

| | Uninoculated Controls | | Inoculated Test Samples | | Retested Inoculated Sample | |
|---|---|---|---|---|---|---|
| Hours | Sample No. | Vial CO₂ to Reference CO₂ Ratio | Sample No. | Vial CO₂ to Reference CO₂ Ratio | Sample No. | Vial CO₂ to Reference CO₂ Ratio |
| 0 | #1 | 1.01 | #2 | 0.64 | — | — |
| 4 | #3 | 1.02 | #4 | 1.45 | #2 | 1.43 |
| 8 | #5 | 1.04 | #6 | 2.31 | #2 | 2.72 |
| 12 | #7 | 1.05 | #8 | 1.86 | #2 | 3.17 |

Figure 3:
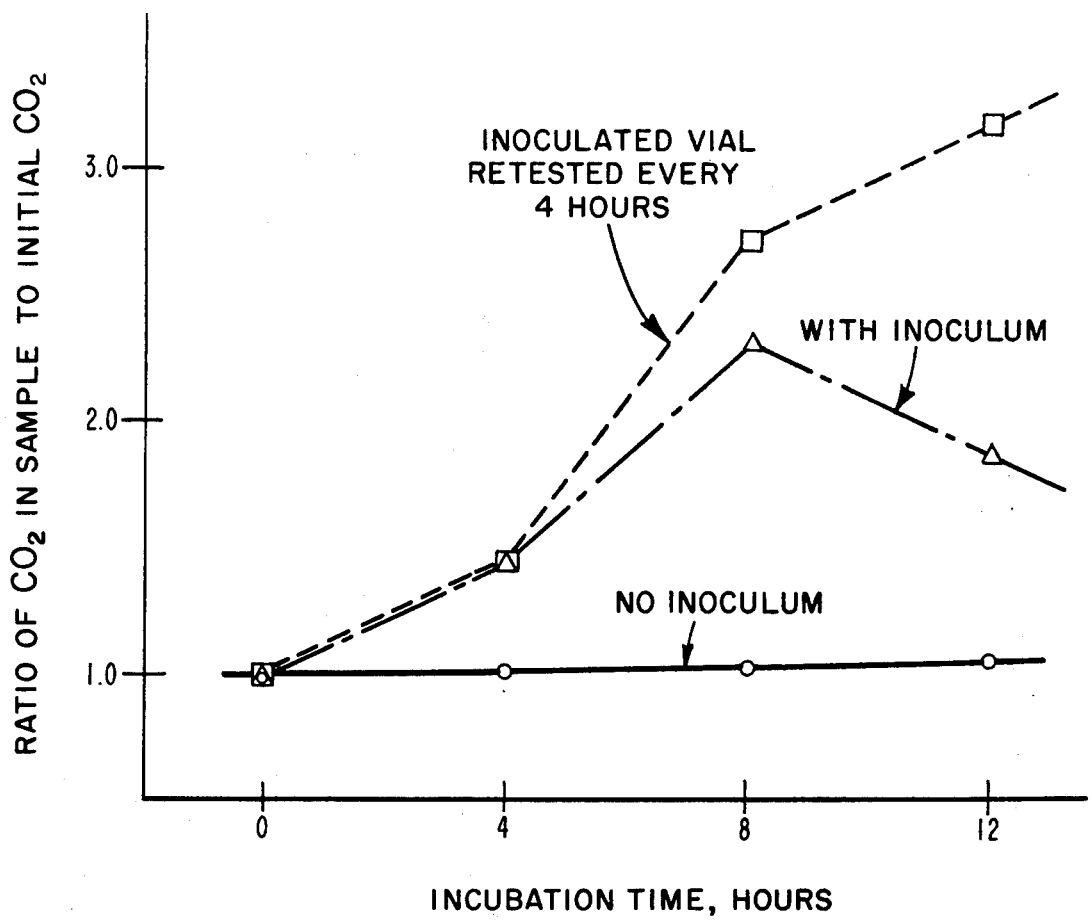
FIG. 3 is a graphic representation of the results from an experiment demonstrating the effectiveness of the method of the invention.

Consideration of FIG. 3 reveals that there is no substantial change in the culture gas carbon dioxide content in the uninoculated control vials, but that in the inoculated vials the concentration of carbon dioxide in the culture gas increases significantly thereby indicating the presence of a biologically active agent. Unambiguously positive results are observed after only 4 hours incubation. The low value of the initial $CO_2$ measurement of vial No. 2 is thought to be a measurement error and was disregarded in preparing FIG. 3. No cause is presently known for the apparently anomalous carbon dioxide value in vial No. 8.

EXAMPLE III

A sterile vial fitted with a dual closure system comprising a threaded cap and an opening closed with a rubber septum is partially filled with tryptic soy broth, and the vial and culture medium are sterilized. The threaded closure is opened, and a small amount of processed baby food is introduced into the vial after which the threaded closure is resealed. The gas space within the vial is flushed with a fresh culture gas, and a sample of the culture gas is taken for analysis of the carbon dioxide content. The vial and its contents are thereafter incubated for a period of 48 hours at 30° C after which a second sample of the culture gas is taken for analysis of the carbon dioxide content. The post-incubation culture gas sample contains an appreciably greater amount of carbon dioxide than the initial culture gas sample indicating bacterial contamination of the baby food.

The foregoing embodiments have been described solely for purposes of exemplification and not by way of limitation. Since modifications of the disclosed embodiments may occur to persons skilled in the art, the scope of the invention is to be limited solely by the scope of the appended claims.

What is claimed is:

1. A method for detecting the presence of bacteria comprising the steps of:
   a. providing a sealable, sterile container containing a sterile, non-radioactive culture medium comprising at least one substrate material convertible to a selected gaseous product by direct bacterial action, said container further containing a quantity of culture gas comprising an inert reference gas in said container above said culture medium, said container comprising means to facilitate the introduction of a sample of test material into the container;
   b. determining the initial ratio of the selected product gas to the reference gas in said culture gas;
   c. introducing a sample of material to be tested for bacterial activity into the container and sealing the container;
   d. subjecting the sealed container to conditions conducive to bacterial growth for a predetermined period of time sufficient for fermentation of the culture medium to produce the selected gaseous product;
   e. thereafter withdrawing a sample of the culture gas from said sealed container and determining the ratio of the selected product gas to reference gas in the culture gas sample; and
   f. comparing the ratio of the selected product gas to reference gas in the culture gas sample to the initial ratio of selected product gas to reference gas in the culture gas.

2. A method as recited in claim 1 wherein said sealed container is subjected to conditions conducive to bacterial growth for a period of between about 1 and about 8 hours.

3. A method as recited in claim 2 wherein said sealed container is subjected to conditions conducive to bacterial growth for a period between about 2 to about 4 hours.

4. A method as recited in claim 1 wherein the culture medium comprises tryptic soy broth.

5. A method as recited in claim 1 wherein the sealed container is subjected to conditions conducive to bacterial growth by maintaining the contents at a temperature lying in the range from about 35° C to about 37° C and agitating the culture medium.

6. A method as recited in claim 1 wherein the ratio of the product gas to reference gas is determined by analyzing the composition of the culture gas with a mass spectrometer.

7. A method as recited in claim 1 wherein the ratio of the product gas to reference gas is determined by analyzing the composition of the culture gas with a gas chromatograph.

8. A method as recited in claim 1 wherein the ratio of the product gas to reference gas is repeatedly measured at periodic intervals during the period of subjection to conditions conducive to bacterial growth and each measurement is compared to the initial ratio whereby to follow the bacterial growth in the test material with respect to time.

9. A method as recited in claim 1 wherein said sample of material to be tested is a fluid, said means to facilitate the introduction of said test material into the container comprises a self-sealing rubber septum, and the introduction of said test sample into said container is effected by injecting said sample through said septum with a hypodermic syringe.

10. A method as recited in claim 1 wherein said sample of material to be tested is a solid, and said means to facilitate the introduction of said test material into the container comprises an aperture through the wall of the container fitted with a tightly sealing removable cap.

11. A method for detecting the presence of bacteria comprising the steps of:
   a. providing a sealable, sterile container containing a sterile, non-radioactive culture medium comprising at least one carbon compound fermentable to produce $CO_2$, said container further containing a quantity of culture gas comprising less than about 2% of an inert reference gas in said container above the culture medium, said container comprising means to facilitate the introduction of a sample of test material into the container;
   b. determining the initial ratio of $CO_2$ to reference gas in said culture gas;
   c. introducing a sample of material to be tested for bacterial activity into said container and sealing said container;
   d. subjecting the sealed container to conditions conducive to bacterial growth for a predetermined period of time sufficient for fermentation of said carbon compound to produce $CO_2$;
   e. thereafter withdrawing a sample of said culture gas from said sealed container and determining the ratio of $CO_2$ to reference gas in said culture gas sample; and
   f. comparing the ratio of $CO_2$ to reference gas in said culture gas sample to the initial ratio of $CO_2$ to reference gas in said culture gas.

12. A method as recited in claim 11 wherein a series of samples of culture gas are withdrawn from said container at periodic intervals and the ratio of $CO_2$ in each sample to the initial concentration of $CO_2$ in the culture gas is determined to thereby determine the relative presence of $CO_2$ in the culture gas in relation to the amount of time that the sample and culture medium have been exposed to conditions conducive to bacterial growth.

13. A method as recited in claim 11 wherein the ratio of $CO_2$ to reference gas is determined by taking a mass spectrum of the culture gas and comparing the magnitude of M/e peak 44 to the magnitude of the M/e peak corresponding to the molecular weight of the reference gas.

14. A method as recited in claim 11 wherein said reference gas is argon.

15. A method as recited in claim 14 wherein the ratio of $CO_2$ to argon is determined by taking a mass spectrum of the culture gas and comparing the magnitude of M/e peak 44 to the magnitude of M/e peak 40.

* * * * *